US006409759B1

(12) United States Patent
Peredo (10) Patent No.: US 6,409,759 B1
(45) Date of Patent: Jun. 25, 2002

(54) HARVESTED TISSUE HEART VALVE WITH SEWING RIM

(75) Inventor: Mario Osvaldo Vrandecic Peredo, Belo Horizonte (BR)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 09/475,525

(22) Filed: Dec. 30, 1999

(51) Int. Cl.$^7$ .................................................. A61F 2/24
(52) U.S. Cl. ...................... 623/2.13; 623/900
(58) Field of Search ............................. 623/2.13, 2.38, 623/2.39, 2.4, 2.41, 2.42, 900

(56) References Cited

U.S. PATENT DOCUMENTS

| | | | |
|---|---|---|---|
| 3,130,418 A | 4/1964 | Head et al. ........................ 3/1 |
| 4,035,849 A | 7/1977 | Angell et al. ..................... 3/1.5 |
| 4,261,342 A | 4/1981 | Aranguren Duo .............. 128/1 |
| 4,769,032 A | 9/1988 | Steinberg ........................ 623/2 |
| 4,960,424 A | 10/1990 | Grooters ......................... 623/2 |
| 5,156,621 A | 10/1992 | Navia et al. .................... 623/2 |
| 5,197,979 A | 3/1993 | Quintero et al. ............... 623/2 |
| 5,306,296 A | 4/1994 | Wright et al. ................... 623/2 |
| 5,336,258 A | 8/1994 | Quintero et al. ............... 623/2 |
| 5,415,667 A | 5/1995 | Frater ............................. 623/2 |
| 5,450,860 A | * | 9/1995 | O'Connor ................... 128/898 |
| 5,554,184 A | 9/1996 | Machiraju ....................... 623/2 |
| 5,662,704 A | 9/1997 | Gross | |
| 5,733,331 A | * | 3/1998 | Peredo ........................... 623/2 |
| 5,824,067 A | * | 10/1998 | Gross ............................. 623/2 |
| 5,910,169 A | 6/1999 | Peredo ........................... 623/2 |
| 6,045,576 A | * | 4/2000 | Starr et al. ..................... 623/2 |
| 6,074,417 A | 6/2000 | Peredo ........................... 623/2 |

FOREIGN PATENT DOCUMENTS

| | | |
|---|---|---|
| DE | 3614292 | 11/1987 |
| DE | 4234127 | 5/1994 |
| WO | WO 00/44312 | 8/2000 |

OTHER PUBLICATIONS

"New Horizons and the Future of Heart Valve Bioprostheses" by, Vetter et al., First Edition, 1994, pp. 93–104.

(List continued on next page.)

*Primary Examiner*—David J. Isabella
*Assistant Examiner*—Urmi Chattopadhyay
(74) *Attorney, Agent, or Firm*—Hallie A. Finucane; Patterson, Thuente, Skaar & Christensen, P.A.; Peter S. Dardi (57) ABSTRACT

A heart valve prosthesis can be formed with a harvested tissue heart valve and a sewing rim that extends outwardly from the annulus of the harvested heart valve for easier attachment of the prosthesis. The heart valve prosthesis can further include a belt that extends along the annulus to provide further support to the valve annulus. A single piece of pericardial tissue can be used to form the sewing rim, belt and a collar that envelopes the edge of the annulus. The harvested heart valve prosthesis can have the diameter of its annulus adjusted using pledgeted suture prior to the application of additional support structures such as the belt, sewing rim and collar.

28 Claims, 4 Drawing Sheets

OTHER PUBLICATIONS

"Porcine Stentless Mitral Heart Valve Substitute: Short Term Clinical Data" by, Peredo et al., J. Cardiovascular Surg. 1994; vol. 35 (Suppl. 1 to No. 6), pp. 41–45.

"Transplante De Valva Mitral Heteróloga. Nova Alternativa Cirugica: Estudo Clínico Inicial" by, Peredo et al., Rev. Bras. Cir. Cardiovascular vol. 8, No. 2: pp. 83–90, 1993. (English Abstract).

"A New Approach for Mitral Valve Replacement" by, Peredo et al., Heterologous Stentless Mitral Valve Transplant. Cor. European 3(3) 130–133, 1994.

"Anatomically Complete Heterograft Mitral Valve Substitute: Surgical Technique and Immediate Results" by, Peredo et al., The Journal of Heart Valve Disease, Nov. 1992, vol. 1, No. 2, pp. 254–259.

"Heterologous Mitral Valve Transplant, New Alternative for Mitral Replacement: One Year Clinical Follow–up" by, Peredo et al., Heart Surgery—1993; "Casa Editrice Scientifica Internazionale" Ed. Luigi C. D'Alessandro, Chapter 7, pp, 57–68.

International Search Report (PCT/US00/42199) dated Oct. 12, 2001.

* cited by examiner

HARVESTED TISSUE HEART VALVE WITH SEWING RIM

BACKGROUND OF THE INVENTION

The invention relates to prosthetic heart valves. More particularly, the invention relates to prosthetic heart valves for the replacement of damaged. mitral or tricuspid heart valves.

Heart valve insufficiency can be a debilitating and possibly life threatening condition. For example, heart valve regurgitation, i.e., backward leakage of blood at a heart valve, results in reduced pumping efficiency. With respect to mitral valve. regurgitation, compensatory mechanisms such as hypeirtrophy and dilation of the ventricle suggest early treatment to prevent progressive deterioration of ventricular function. Diagnosis of mitral regurgitation can be performed using visualization with transesophageal echocardiography or by echocardiography. In particular, defective leaflet coaptation and the site and direction of he regurgitant flow can be examined to evaluate likely modes of failure.

Mitral valve prolapse, i.e., myxomatous degeneration of mitral valve leaflets, is the most common cause of mitral regurgitation in North America. Rheumatic heart disease was the most common cause of mitral regurgitation in the United States thirty years ago and is still the most common cause of mitral regurgitation in developing countries. Chronic rheumatic heart disease results in retraction, deformity and rigidity of one or both mitral valve cusps as well as structural abnormalities in the commissures, chordae tendineae and papillary muscles. Ischemic mitral regurgitation (IMR), i.e., anemia of the valve tissue due to reduced arterial blood flow feeding the valve tissue, is the second most common cause of mitral valve regurgitation. Studies suggest that annular irregularities and posterior papillary muscle fibrosis with scarring of the underlying ventricular wall may be associated with IMR.

Many cases of mitral regurgitation can be repaired by modifications of the original valve in a procedure generally referred to as valvuloplasty. For example, one repair technique uses an annuloplasty ring to provide structural support to the natural annulus of the native valve. For severe cases of heart valve damage, however, reconstructive valvular surgery may not be possible. In such cases, valve replacement may be required.

Physicians use a variety of prostheses to correct problems associated with the cardiovascular system, especially the heart. For example, the ability to replace or repair diseased heart valves with, prosthetic devices has provided surgeons with a method of treating heart valve deficiencies due to disease and congenital defects. A typical procedure involves removal of the native valve and surgical replacement with a prosthetic heart valve.

Both mechanical heart valve prostheses and tissue based heart valve bioprostheses have been used to replace damaged heart valves. Mechanical heart valves have the advantage of better durability, but patients with mechanical heart valves generally are required to use anticoagulants throughout their lifetimes. Anticoagulants have associated risks, such as hemorrhages, embolism and thromboembolism. Tissue based bioprostheses do not require the long term use of anticoagulants due to a lower incidence of thromboembolism.

SUMMARY OF THE INVENTION

In a first aspect, the invention pertains to a heart valve prosthesis comprising a harvested tissue heart valve with integral leaflets. The heart valve has an annulus at one end of the valve, and a sewing rim extends outwardly from the annulus.

In another aspect, the invention pertains to additional embodiments of a heart valve prosthesis comprising a harvested tissue heart valve with integral leaflets. The heart valve has an annulus at one end of the valve, and a belt secured around at least a substantial portion of an outer circumference of the annulus of the harvested tissue heart valve.

In a further aspect, the invention pertains to still further embodiments of a heart valve prosthesis comprising a harvested tissue heart valve with integral leaflets. The harvested tissue heart valve has an annulus at one end of the valve, and pledgeted suture constricts a portion of the circumference of the annulus.

Moreover, the invention pertains to a method of producing a heart valve prosthesis comprising a harvested tissue heart valve with integral leaflets, the heart valve having an annulus at one end of the valve, the method comprising attaching a sewing rim extending outward from the surface annulus of the harvested tissue heart valve.

DETAILED DESCRIPTION OF THE ILLUSTRATIVE EMBODIMENTS

An improved replacement heart valve or bioprosthesis includes a sewing rim extending from the annulus along a substantial portion of its circumference and a support ring or belt positioned to support the base of the annulus. The bioprosthesis generally is formed from a harvested tissue heart valve with intact leaflets. In preferred embodiments, a single structure, such as a piece of pericardial tissue, is used to form a collar over the valve annulus, the sewing rim and the belt. Also, the diameter of the annulus of the valve can be reduced using suture prior to the application of the collar. The resulting heart valve bioprosthesis corrects for dilation of the annulus following harvesting of the valve from a donor and reduces the risk of heart valve insufficiency following implantation. "Bioprosthesis" is used in a broad sense to include bioprosthetic heart valves comprised of a natural material component that is joined together with other natural or synthetic materials to manufacture the replacement heart valve.

The improved features of the bioprosthetic valves described herein are suitable for use on atrio ventricular valves, i.e., mitral valves and tricuspid valves, that are constructed using a harvested tissue valve. The harvested valves can be treated appropriately prior to implantation, as described further below. Generally, the bioprosthetic valves are stentless, i.e., a support stent is not used. While the improved features are particularly advantageous for the production of bioprosthetic atrio ventricular valves, at least the improved sewing rim feature can be used advantageously with a bioprosthetic aortic valve. Aortic valves have a simpler structure without the presence of chordae tendineae.

The bioprosthetic valves can be formed using a procured or harvested homograft tissue valve, i.e., a valve from a donor of the patient's species, or a xenograft tissue valve, i.e., a valve from a donor of a different species than the patient. Harvested mitral or tricuspid valves preferably include intact chordae tendineae attached to a portion of papillary muscle of the donor. Even though the bioprosthetic valves of the invention can be mitral valves or tricuspid valves, the discussion below focuses on mitral valves. Mitral valve bioprostheses can be implanted into patient as a replacement for either a mitral or tricuspid valve. Similarly, tricuspid valves incorporated into a bioprosthesis, in principle, can be used to replace damaged mitral or tricuspid valves. Preferably, prostheses formed from harvested mitral valves are used to replace damaged mitral valves, and prostheses formed from harvested tricuspid valves are used to replace tricuspid valves.

In preferred embodiments, the harvested valves are processed to introduce three improved features. First, the harvested valve is secured around its circumference to reduce or maintain the diameter of the annulus. This reduction of the circumference corrects for expansion of the valve annulus that results due to the removal of native structural support following the harvesting of the valve.

Second, a sewing rim is formed that extends outwardly from the surface of the valve along the side of the annulus around the circumference of the valve. By forming the sewing rim along the side of the annulus, the risk of damaging the leaflets during implantation by inserting the suture needle through the leaflets is decreased in comparison with using a collar located at the edge of the annulus as a sewing cuff. The sewing rim can be formed from a portion of material used in forming a collar that is folded over the edge of the annulus Third, a support ring or belt that is a functional equivalent of an annuloplasty ring is constructed around the circumference along the side of the annulus to support the annulus of the valve following implantation. This belt may eliminate the need for using a separate annuloplasty ring when surgically implanting the valve. The belt can be constructed from the same piece of material used to form the collar and sewing rim.

The collar, sewing rim and belt can be constructed from a variety of natural and synthetic biocompatible materials. In a preferred embodiment, pericardial tissue is used to form the collar, sewing rim and belt. For example, the belt can be formed from rolled-up pericardial tissue at the end of a sheet of the pericardial tissue and the sewing rim can be formed from a piece of folded pericardial tissue between the belt and the portion of tissue that is folded over the edge of the annulus to form the collar.

To form the preferred embodiments of the bioprosthetic heart valves, the annulus of the harvested valve is sutured to draw in the circumference and achieve the desired annular circumference prior to addition of the collar, sewing rim and belt. After suturing the annulus, the collar, sewing rim and/or belt are attached to the sutured annulus of the harvested valve. If the collar, sewing rim and belt are formed from a single section of material, the procedure properly positions each of the elements at the appropriate location on the tissue heart valve. Markings can be placed at suitable locations along the collar, sewing rim and/or belt to assist the physician with properly positioning and implanting the valve during the implantation process.

Structure of Improved Heart Valve Bioprostheses

The improved heart valve bioprosthesis includes a procured or harvested natural heart valve that is modified before implantation. At least a portion of a supplemental support structure preferably supports the annulus of the harvested valve. The supplemental support structure is generally elastic and flexible with respect to the shape of the annulus while maintaining a desired circumference of the annulus. The support structure generally extends around a substantial portion of the circumference of the annulus, preferably at least a majority of the circumference, and more preferably extends around the entire circumference. For mitral and tricuspid valves, additional supports can be used for the papillary muscle sections attached to chordae. The heart valve bioprosthesis is stentless.

The supplemental support structure can be formed from natural or synthetic materials, as described in detail below. The supplemental support structure can assist with the sizing and implantation of the bioprosthesis as well as improving the durability and performance of the bioprosthesis. To form a mitral or tricuspid heart valve bioprosthesis, a mitral or tricuspid heart valve structure is harvested from a donor. The procured heart valve prosthesis can be treated prior to additional processing, as described further below.

Figure 1:
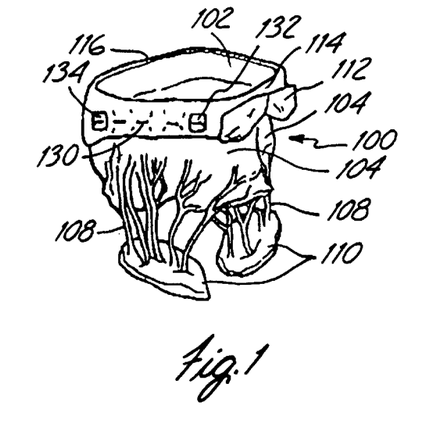
FIG. 1 is a side perspective view of a harvested heart valve with a sutured annulus viewed along the posterior medial segment of the annulus.
Figure 2:
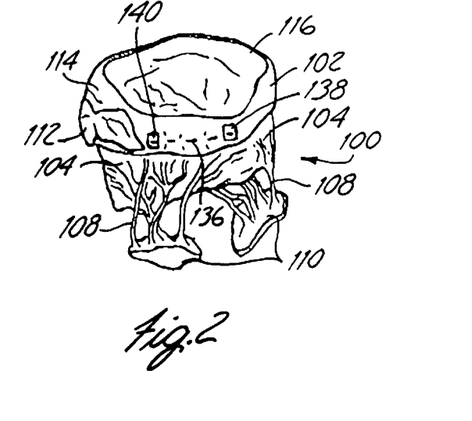
FIG. 2 is a side perspective view of the harvested heart valve of FIG. 1 viewed along the antero-lateral aspect of the annulus.
Figure 3:
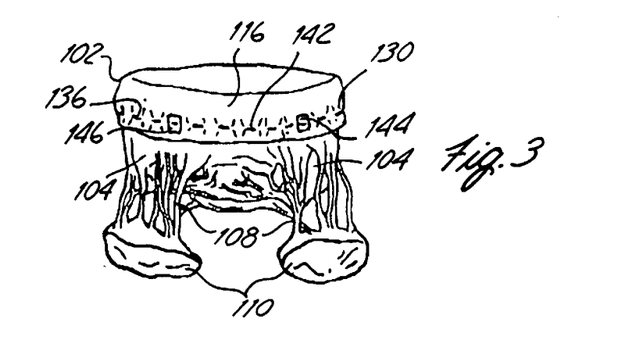
FIG. 3 is a side perspective view of the harvested heart valve of FIG. 1 viewed along the posterior mitral annulus.

Referring to FIGS. 1–3, harvested mitral heart valve 100 preferably includes an annulus 102, leaflets 104, which connect to annulus 102, chordae tendineae 108 which extend between leaflets 104 and portions of papillary muscle 110 of chordal origin from the host animal. The leaflets 104, chordae 108 and chordal origin papillary muscle 110 form a complete subvalvular apparatus. Annulus 102 includes a remaining portion of porcine aortic cusp 112 at the anterior mitral annulus 114.

Figure 4:
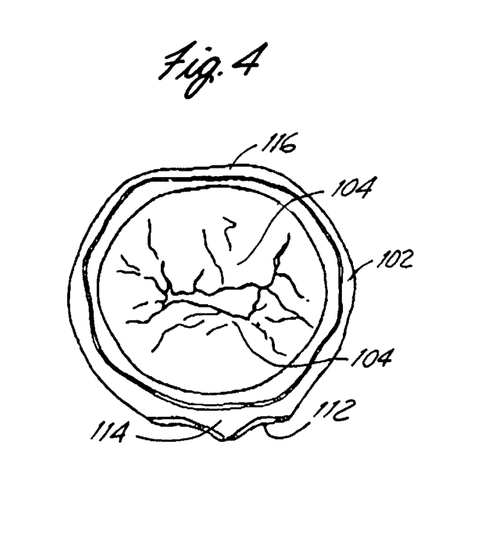
FIG. 4 is a top plan view of a harvested mitral valve exhibiting mitral valve insufficiency.

Mitral heart valves often increase in valve diameter following harvesting of the valve from the donor due to the lack of support for the valve. Mitral annular enlargement takes place almost entirely in the region of the posterior mitral annulus 116. Posterior mitral annulus 116 is formed mostly with atrial muscle, while the region of anterior annulus 114 is supported by the fibrous skeleton, i.e., mitro-aortic tendinous tissue. Enlargement of the valve diameter can impair proper valve coaptation, as shown in FIG. 4, where leaflets 104 do not meet properly or completely close in the center of the valve. Improper closure of the valve can result in significant malfunctioning of the valve, which can require valve replacement.

In preferred embodiments, the diameter of annulus 102 of valve 100 is reduced prior to the addition of other support structures for annulus 102, such as with suture. While this suturing can be formed with a single piece of suture, it is preferred to form the sutured annulus with a plurality of suture segments to avoid introducing excess tension that can result if a single suture is used. Also, it is preferred to use pledgeted, monofilament suture in which pledgets at each end of the suture help to secure a section of suture under tension without damaging the annulus. Other methods to draw in or reduce the diameter of the annulus can be used, such as clipping or stapling.

Figure 5:
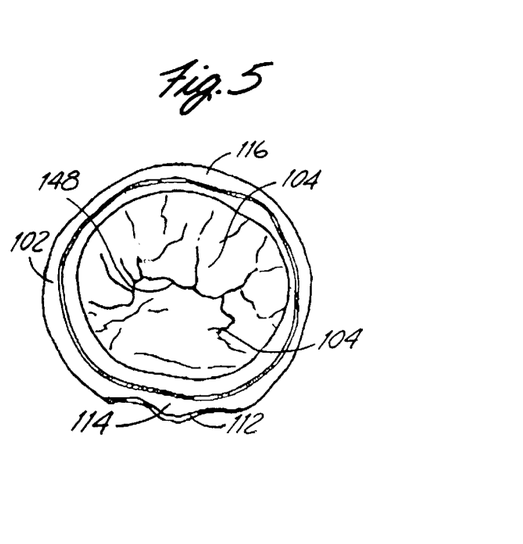
FIG. 5 is a top plan view of a harvested mitral valve wherein the leaflets close properly.

A particularly preferred embodiment is shown in FIGS. 1–3 where three sections of pledgeted, monofilament suture are used to reduce the diameter of the valve. Referring to FIG. 1, a first segment of suture 130 with pledgets 132, 134 is placed on the lateral segment corresponding to the posterior medial segment of the annulus. Referring to FIG. 2, a second segment of suture 136 with pledgets 138, 140 is placed along the antero-lateral aspect of annulus 102. Referring to FIG. 3, a third segment of suture 142 with pledgets 144, 146 is placed along the posterior mitral annulus 116. A running or continuous suture can be used, for example, in the suture placement. Appropriate reduction of the valve diameter results in proper valve leaflet coaptation, i.e., full mitral valve leaflet closure, at leaflet junction 148, as shown in FIG. 5. Leaflet coaptation can be observed during the suturing process to ensure that proper tension is applied to result in correct coaptation. Furthermore, with harvested valve 100 having an adjusted diameter, the physician can directly size the valve for implantation into the patient.

While the valve diameter preferably is reduced using suture, as described above, excessive manipulation of the valve during implantation can result in enlargement of the valve diameter due to deterioration of the effectiveness of the suture. Thus, a collar preferably is applied over the valve annulus to further maintain the valve annulus at the properly selected annulus diameter. The pledgeted suture sewn into the annulus to reduce the valve diameter and the collar together create a stable and durable valve bioprosthesis with an appropriately sized annulus.

An annulus collar has been used to reduce the annular diameter, as described in U.S. Pat. No. 5,733,331 to Peredo, entitled "Total Mitral Heterologous Bioprosthesis to be Used in Mitral or Tricuspid Heart Replacement," incorporated herein by reference. The use of pledgeted suture sewn directly into the annulus combined with an annular collar and belt, however, offers significant advantages. First, the pledgeted suture can be used conveniently to distribute the desired tension to provide a competent valve. In addition, the belt and collar provide added protection against undesirable enlargement of the valve diameter prior to and after implantation.

As noted above, along with an annulus collar, a preferred heart valve bioprosthesis has a sewing rim along the side of the annulus and a belt supporting the base of the annulus. A preferred heart valve bioprosthesis 160 is shown in FIGS. 6–10. Mitral valve bioprosthesis 160 includes a collar 162, a sewing rim 164 and a belt 166 secured over the annulus 102 of the harvested mitral valve. Although collar 162, sewing rim 164 and belt 166 can be applied individually or with two of the elements formed together, in preferred embodiments, collar 162, sewing rim 164 and belt 166 form a single, unified supplemental support structure 168 at annulus 102. The diameter of the valve bioprosthesis is selected to obtain proper closure of the leaflets, as shown in FIG. 10.

Collar 162 envelops the edge of annulus 102, being secured with suture both on the inside of annulus 102 and the outside of annulus 102. Sewing rim 164 includes an extension of material extending outwardly, preferably generally perpendicular, from the surface of annulus 102. Sewing rim 164 can be formed, for example, from a fold of material, as described further below. Sewing rim 164 generally extends at least about 2 mm from the surface of the annulus, preferably from about 2 mm to about 4 mm, and more preferably from about 2 mm to about 3.5 mm from the surface of the annulus. The sewing rim preferably has a thickness less than about 2 mm, and preferably from about 1.3 mm to about 1.8 mm.

Belt 166 is a strong, relatively resilient structure, which obviates the need for the implantation of a separate annuloplasty ring. Belt 166 eliminates valve dilation and changes in diameter, and maintains competency of the valve following implantation. Belt 166 can be formed from rolled up material, or from a fold of material covering a flexible ring structure, such as a polymer ring or metal wire, to form belt 166, or from the separate attachment of a belt structure.

Figure 8:
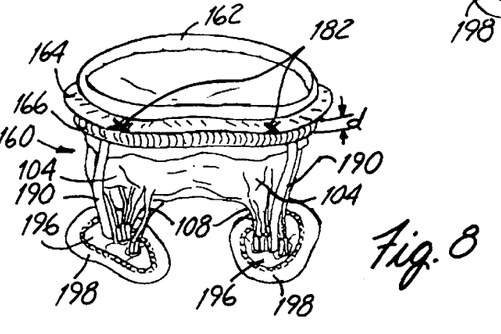
FIG. 8 is a side perspective view of the mitral heart valve prosthesis of FIG. 6 viewed from the anterior side of the annulus.

Belt 166 can have any reasonable cross sectional shape, such as round or rectangular, and the cross sectional shape can vary from one portion of the belt to other portions of the belt. Belt 166 generally has a thickness or distance "d" along the surface of the annulus, as shown in FIG. 8, of at least about 1.5 mm, preferably from about 1.5 mm to about 4 mm and more preferably from about 2 mm to about 3 mm. Similarly, belt 166 generally extends outwardly from the annulus surface at least about 1.5 mm, preferably from about 1.5 mm to about 4 mm and more preferably from about 2 mm to about 3 mm.

Figure 6:
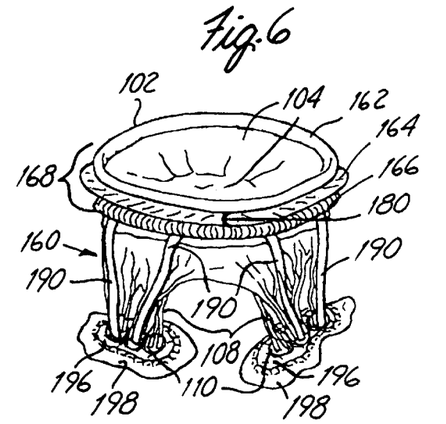
FIG. 6 is a side perspective view of a mitral heart valve prosthesis with a collar sewing rim and belt viewed along the posterior side of the annulus.
Figure 9:
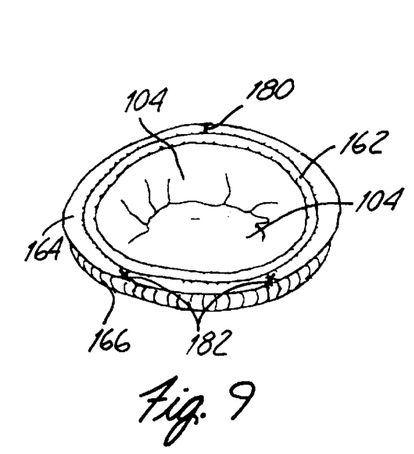
FIG. 9 is a top perspective view of the bioprosthetic valve of FIG. 6.
Figure 10:
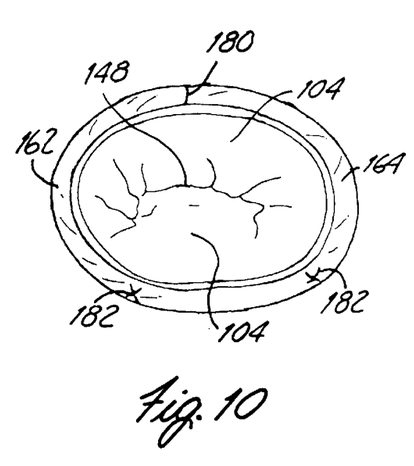
FIG. 10 is a top plan view of the bioprosthetic valve of FIG. 6.

To assist the surgeon with correct placement of the heart valve during implantation, a marker 180 can be placed at the mid-position of the posterior mitral annulus, as shown in FIGS. 6, 9 and 10. Marker 180 can be made, for example, with suture. Similarly, markers 182 can be placed to denote each trigone, as shown in FIGS. 8–10. Markers 182 should be visually distinguishable from marker 180, for example, by the use of different colors and/or by the use of a different shape, such as an "x" for the trigone markers 182. The trigone markers can be used by the surgeon to guide the attachment of the heart valve bioprosthesis to the patient's annulus during implantation.

Figure 7:
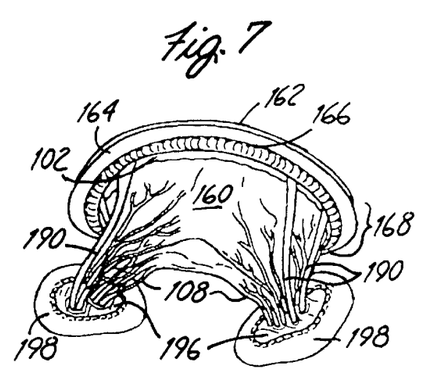
FIG. 7 is a bottom perspective view of the mitral heart valve prosthesis of FIG. 6.

Further structural support can be provided with strips 190 that connect annulus 102, support structure 168, or a component of support structure 168, with one of the chordal origin papillary muscles sections 110. Strips 190 decrease the stress on chordae 108 during the attachment procedure. Strips 190 generally are attached in a way that maintains the natural angulation and spacial geometry between the papillary muscle sections 110 and chordae 108. Strips 190 are of an appropriate length to maintain a uniform chordal tension such that the stress load is distributed between strips 190 and chordae 108 to increase valve durability. In preferred embodiments, a plurality of strips 190 are used with each chordal group. As shown in FIGS. 6–8, a total of four strips 190 are used, with two strips 190 used for each of the two chordal groups.

In preferred embodiments, natural chordae groups are preserved where each group is secured to one or more sections of chordal origin papillary muscle 110. Papillary muscle 110 can be secured in groups with an upper patch 196 and a lower patch 198. The edges of lower patch 198 preferably fold over the edges of upper patch 196. Upper patch 196 is cut-out such that upper patch 196 does not contact the chordae 108. Thus, upper patch 196 does not disrupt the attachment of chordae 108 with papillary muscle 110. Upper patch 196 preferably is sutured to lower patch 198 through papillary muscle 110 to form a secure structure for attachment to the papillary muscle of the patient during implantation. Strips 190, upper patch 196 and lower patch 198 each can be made from tissue, such as a pericardial tissue, or from synthetic material.

Materials for Forming the Heart Valve Bioprosthesis

As described in the previous section, a preferred heart valve bioprosthesis includes a harvested natural heart valve, suture, pledgets, a collar, a belt, a sewing rim, strips connecting the annulus support structure with the chordal origin papillary muscles and patches attached to papillary muscle sections of the harvested valve. Except for the harvested natural heart valve, the remaining materials can be either natural or synthetic. The harvested tissue heart valve can be a homograft valve, i.e., from the same species as the patient, or a xenograft valve, i.e., from a different species than the patient. Thus, for a human patient, a homograft heart valve is removed from a human cadaver. Suitable xenograft mitral heart valve structures for human patients can be, for example, bovine, porcine, canine, seal, kangaroo or from transgenic mammals. Suitable donors have a heart valve of an appropriate size and shape.

Harvested tissue heart valves can be fixed by crosslinking. This provides mechanical stabilization, for example, by preventing enzymatic degradation of the tissue. Crosslinking also removes antigenic sites that could result in the patient's rejection of the bioprosthesis. Glutaraldehyde or formaldehyde typically is used for fixation, but other fixatives can be used, such as epoxides, genipin and other difunctional aldehydes. Xenografts, i.e., prostheses incorporating tissue from a species different from the patient's species, generally are fixed prior to use. Homografts or allografts, i.e., prostheses incorporating tissue of a different individual of the patient's species, may or may not be fixed prior to use. In addition, the bioprostheses can be treated to reduce calcification and/or the risk of microbial infection, and can incorporate other features of tissue engineering.

As noted above, preferred embodiments of the heart valve bioprosthesis include pledgeted suture that secures the diameter of the valve annulus to a diameter approximating the native state. Suitable suture can be formed from biological sources, such as cat gut suture and natural fibers such as cotton and silk, or synthetic materials, such as synthetic polymers. The suture can be mono-filament suture, such as cat gut and Prolene®, or braided (poly-filament suture), such as natural or synthetic fibers formed into yarns. The suture can be absorbable or permanent. The suture preferably comprises permanent monofilament suture, such as Prolene® brand polypropylene suture, which is relatively nonabrasive to tissue.

Pledgets function as an anchoring device in pledgeted suture at each end of the suture. The pledgets help to protect the sutured tissue from tearing. The pledgets can be formed from natural or synthetic materials. Preferred pledgets are formed from crosslinked pericardial tissue. While any reasonable size of pledgets can be used, 2 mm×4 mm pledgets are a convenient size.

As noted above, the collar, sewing rim and belt preferably are produced from a single piece of material. The collar, sewing rim and belt can be produced from natural material, synthetic material, or a combination thereof. Preferred material for the production of a collar, sewing rim and belt includes harvested tissue, and more preferably pericardial tissue. The pericardial tissue section generally is xenograft tissue, especially bovine tissue, that is fixed by crosslinking.

The pericardial tissue or other biocompatible material section is cut to have the desired size to form the collar, sewing rim and belt. Due to varying valve sizes, the biocompatible material section can have a range of sizes with height ranging from about 1 cm to about 2 cm, length ranging from about 3 cm to about 12 cm and thickness ranging from about 0.2 mm to about 0.9 mm. The length of the section corresponds to the circumference of the heart valve bioprosthesis following attachment of the material. The height of the biocompatible material section is used to form the collar, sewing rim and belt.

Figure 11:
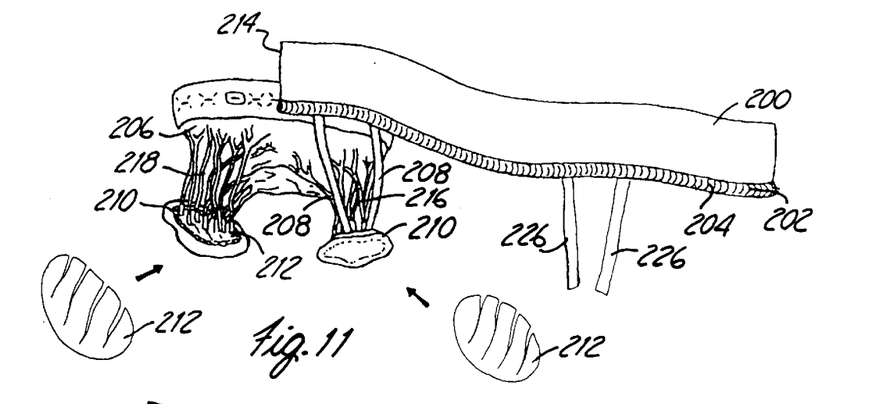
FIG. 11 is a side perspective view of a bioprosthetic heart valve with a pericardial sheet being initially attached to the bioprosthetic valve.

Using a single sheet of pericardial tissue, one long edge of the pericardial tissue can be rolled to form the belt structure of the ultimate bioprosthesis. The tissue preferably is rolled between two and four times, such that the total thickness of the belt ranges from about four times to about 8 times the thickness of a sheet of tissue. Referring to FIG. 11, a section of pericardial tissue 200 includes a portion of rolled tissue 202. Rolled tissue 202, forming a belt, is kept in its rolled configuration by interrupted or continuous mono or multiple filament suture 204.

The sewing rim can be formed during the process of securing the tissue to the valve, as described below. The edge of the tissue opposite the belt is folded over the end of the annulus to form the collar.

As noted above, the papillary muscle patch, pledgets, collar, sewing rim and belt each can be formed from synthetic material, such as natural or synthetic polymers. Polymeric materials can be fabricated from synthetic polymers as well as purified biological polymers. The polymeric materials can be formed into fibers or yarns and then woven into a mesh to form a sheet or other shape. Alternatively, the polymer materials can be molded or cast into appropriate forms.

Appropriate synthetic polymers include, without limitation, polyamides (e.g., nylon), polyesters, polystyrenes, polyacrylates, vinyl polymers (e.g., polyethylene, polytetrafluoroethylene, polypropylene and poly vinyl chloride), polycarbonates, polyurethanes, poly dimethyl siloxanes, cellulose acetates, polymethyl methacrylates, ethylene vinyl acetates, polysulfones, nitrocelluloses and similar copolymers.

Biological polymers can be naturally occurring or produced in vitro by, for example, fermentation and the like. Purified biological polymers can be appropriately formed into a substrate by techniques such as weaving, knitting, casting, molding, extrusion, cellular alignment and magnetic alignment. Suitable biological polymers include, without limitation, collagen, elastin, silk, keratin, gelatin, polyamino acids, polysaccharides (e.g., cellulose and starch) and copolymers thereof.

As noted above, multiple portions of one or more biocompatible materials can be used to form the collar, sewing rim and belt. Two or more portions can be attached together prior to securing the portions to the harvested heart valve. For example, a ring or the like can be fastened, for example with suture, to or in a pericardial sheet to form a belt. The ring can be formed from natural material, i.e., tissue, or synthetic material. The pericardial sheet can then be used to form the collar and sewing rim. The ring is positioned along the pericardial sheet such that it will be located at a desired position for the belt once the components are assembled. For example, the belt can preferably be placed near the bottom long edge of the pericardial sheet such that the belt is located just below the sewing rim after the components are assembled. Similarly, the belt can be fastened near the center of the pericardial sheet such that the belt will be located just above the sewing rim after components are assembled.

Alternatively, the portions can be secured together when attaching the components to the bioprosthesis. A particular component can be sewn to another securing component or directly to the harvested heart valve. For example, a sheet of material can be used to form the collar and sewing rim while an annular structure used for the belt can be sewn directly to the tissue of the harvested heart valve, directly to the material forming the collar and sewing rim, or a combination thereof. Similarly, the collar and sewing rim can be formed from different portions of material, which are attached together or separately secured to the annulus of the harvested heart valve.

Strips are generally connected between the annulus support structure and the papillary muscle section or corresponding patches. These strips can be formed from natural materials, such as tissue, or synthetic materials, such as polymers. The strips can be attached to the annulus support structure or to the harvested heart valve.

The papillary muscle patches can be formed from ore or more materials. For example, an upper patch can be formed from one material while a lower patch can be formed from a second material. Similarly, a single papillary muscle patch can be formed from a combination of multiple materials. While papillary muscle patches are preferably formed from tissue, such as fixed bovine pericardial tissue, papillary muscle patches can be formed from synthetic materials, as described above, or a combination of tissue and synthetic materials.

Formation of the Improved Heart Valve Bioprosthesis

The preferred heart valve bioprosthesis includes pledgeted suture sewn around the annulus of the harvested tissue heart valve. As noted above, it is preferable to use multiple sections, for example three sections, of pledgeted suture to distribute the tension around the circumference of the annulus. The pledgeted suture can be applied by hand where the degree of reduction of the valve circumference is determined by the degree of tension applied with the suture. The amount of tension should result in a competent valve. The suturing process is performed in a way to avoid tissue damage by the suture used to decrease the extent of a particular segment of the valve annulus. The protection given by a bovine pericardial pledget is generally sufficient to prevent tissue laceration by the suture material.

The application of the collar, sewing rim and belt is described in terms of attachment of an integral section of biocompatible material, such as pericardium, that forms all three structures. Approaches for the attachment of alternative structures for formation of the collar, sewing rim and belt can be readily adapted from the following description of the attachment of a single piece of bovine pericardium. Referring to FIG. 11, a section of pericardium 200, such as bovine pericardial material, is positioned relative to harvested tissue heart valve 206 such that strips 208 can be positioned near a group of chordae. Strips 208 are secured to a fragment or fragments of papillary muscle 210 from the transplant donor or to patches 212 supporting papillary muscle 210. Preferably, a first edge 214 of bovine pericardial material 200 is positioned approximately in the middle of the posterior annulus. Patches 212 for providing additional support can be secured to the papillary muscle fragments 210 prior to or after securing strips 208 to papillary muscle fragments 210.

Figure 12:
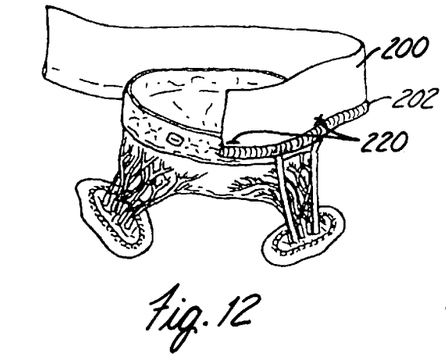
FIG. 12 is a side perspective view of the bioprosthetic heart valve of FIG. 11 wherein a portion of the pericardial sheet is fastened to the valve.
Figure 13:
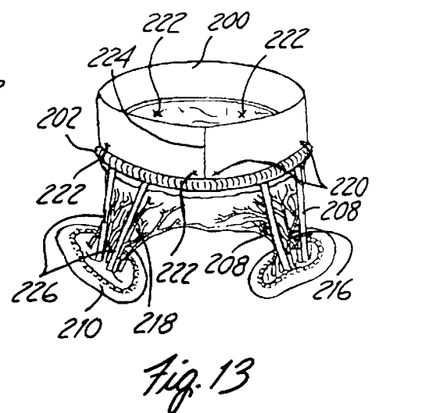
FIG. 13 is a side perspective view of the bioprosthetic heart valve of FIG. 11 wherein the pericardial sheet is fastened around the circumference of the valve.

Suture 220 is applied to tack pericardial material 200 at the correct location with strips 208 positioned appropriately near chordae 216 for attachment to papillary muscle fragments 210 and/or patches 212, as shown in FIG. 12. Pericardial material 200 is wrapped around the remaining portion of the valve circumference and secured with additional suture 222, as shown in FIG. 13. The edges of the pericardial tissue 200 meet at a seam 224 The edges preferably meet essentially flush, forming a seam 224, although seam 224 can be used to adjust the joining of the edges. When the pericardial material 200 is positioned around the circumference of harvested tissue heart valve 206, a second group of strips 226 are positioned for attachment to papillary muscle 210 associated with a second group of chordae 218.

Figure 14:
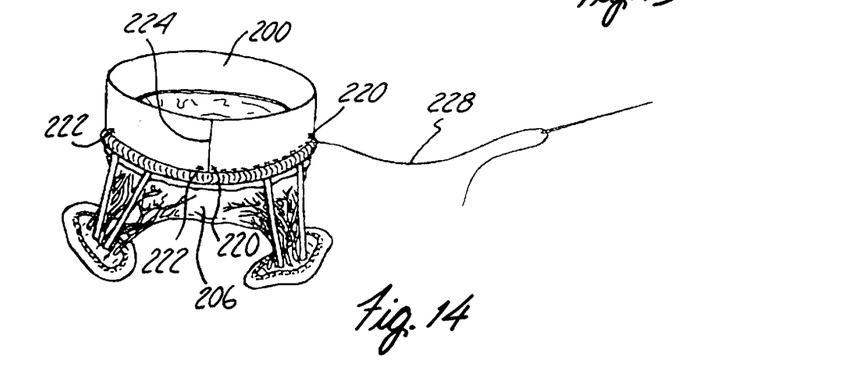
FIG. 14 is a side perspective view of the bioprosthetic heart valve of FIG. 11, wherein the pericardial sheet is being sutured to the bioprosthetic heart valve.

Referring to FIG. 14, pericardial material 200 is attached around the entire annulus with continuous or interrupted sections of mono or multiple filament suture 228. Preferably, the suture is applied just above the belt 202 such that the sewing rim can be formed above the belt. Suture 228 preferably passes through pericardial material 200 and the annulus of harvested tissue valve 206, avoiding the leaflet material.

Figure 15:
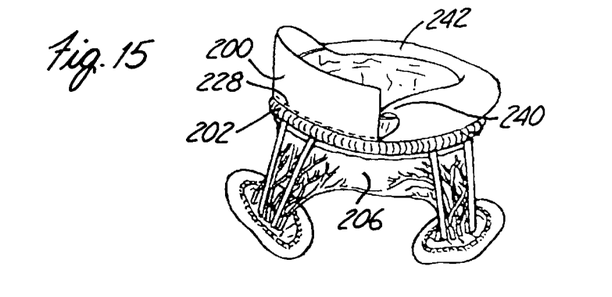
FIG. 15 is a side perspective view of the bioprosthetic valve of FIG. 14 wherein the pericardial sheet is being folded to form a collar.
Figure 16:
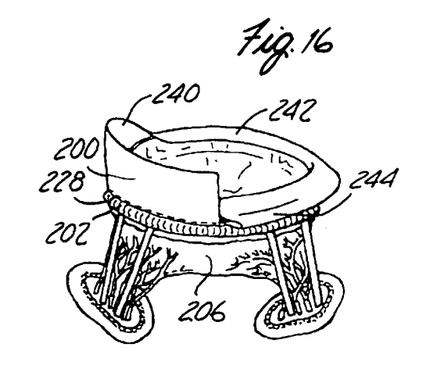
FIG. 16 is a side perspective view of the bioprosthetic valve of FIG. 15 wherein the pericardial sheet is further folded to form a sewing rim.
Figure 17:
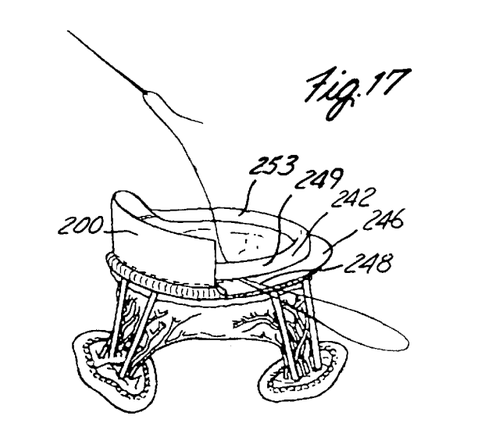
FIG. 17 is a side perspective view of the bioprosthetic valve of FIG. 16 wherein the pericardial sheet is being sutured to secure the collar.

The remaining pericardial material 200 is folded to form the collar and sewing rim. Referring to FIGS. 15 and 16, the top portion 240 of pericardial material 200 is used to form the collar 242. A portion of material 244 between collar 242 and suture 228 is folded to form the sewing rim 246, as shown in FIG. 17.

Figure 18:
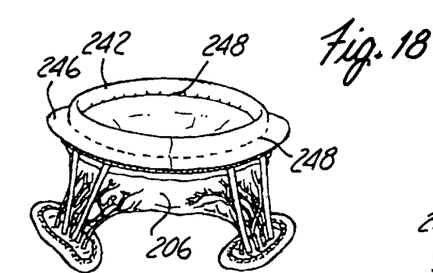
FIG. 18 is a side perspective view of the bioprosthetic valve of FIG. 17 wherein the collar is secured by suture applied around the circumference of the valve.

Collar 242 is secured with suture 248. To complete the stitching, suture 248 is passed from the outer edge 249 of collar 242 through the annulus of harvested tissue valve 206 through the inner edge 253 of collar 242, as shown in FIG. 17, although suturing could be done separately on both inner edge 253 and outer edge 249. Suturing is continued around the circumference of the valve with one or more sections of suture 248 to complete formation of collar 242, as shown in FIG. 18.

Figure 19:
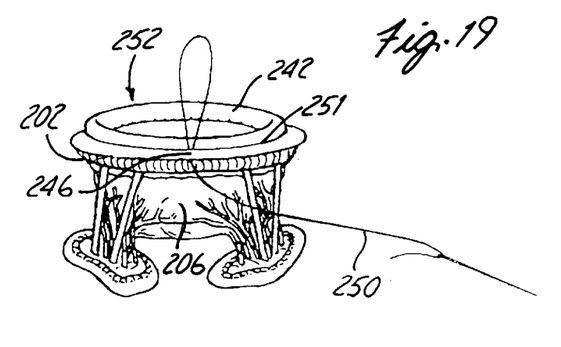
FIG. 19 is a side perspective view of the bioprosthetic valve of FIG. 18 wherein suture is being applied to the sewing rim.

To complete formation of sewing rim 246, one or more sections of suture 250 are sewn through the inner edge 251 of sewing rim 246. Preferably, suture 250 passes from top surface of sewing rim 246 through the bottom surface of sewing rim 246, as shown in FIG. 19. Suture 250 generally goes around the whole circumference of sewing rim 246. This completes the formation of the collar 242, sewing rim 246 and belt 202 structures on the heart valve bioprosthesis 252. In some embodiments, sewing rim 246 is positioned around the entire circumference of valve 206, and collar 242 and belt 202 can be around less than the entire circumference, if desired.

Storage, Distribution and Use of Bioprosthesis

Following formation of the heart valve bioprosthesis, the bioprosthesis can be stored. The bioprosthesis generally is stored in a moist environment such that the tissue components do not become dried out. The tissue can undergo irreversible degradation if it becomes dried out. In preferred storage approaches, the bioprosthesis is immersed in a liquid during storage.

Preferred storage techniques minimize the risk of microbial contamination. For example, the biocompatible material can be stored in a sealed container with sterile buffer and/or saline solution. Even though the bioprosthesis is stored in a sterile environment, the storage time can be limited appropriately to keep any possible degradation of the bioprosthesis with the passage of time to acceptable levels.

For distribution the bioprosthesis generally is placed in sealed and sterile containers. The containers can be dated such that the date reflects the maximum advisable storage time accounting for possible deterioration of the heart valve bioprosthesis. The containers generally are packaged with instructions for the implantation of the heart valve bioprosthesis along with desired and/or required labels. The containers are distributed to health care professionals for surgical implantation of the prostheses. The implantation is performed by a qualified health care professional. The surgical implantation generally involves the replacement of damaged tissue with the bioprosthesis.

As noted above, in preferred embodiments, an annuloplasty ring is not needed since the belt is secured about the circumference of the replacement valve annulus. Sizing can be performed, as with any prosthetic valve, by comparing the sewing rim to the patients native annulus. The improved valves described herein are particularly convenient for implantation without risking damage to delicate leaflets and for maintaining valve compentency.

The embodiments described above are intended to be illustrative and not limiting. Additional embodiments are within the claims below. Although the present invention has been described with reference to preferred embodiments, workers skilled in the art will recognize that changes may be made in form and detail without departing from the spirit and scope of the invention.

What is claimed is:

1. A heart valve prosthesis comprising:
   a harvested tissue heart valve with integral leaflets, the heart valve having an annulus at one end of the valve; and
   a sewing rim having an extension of material extending outwardly from the surface of the annulus.

2. The heart valve prosthesis of claim 1 wherein the harvested tissue heart valve comprises a harvested xenograft mitral he rat valve.

3. The heart valve prosthesis of claim 2 wherein the harvested xenograft mitral heart valve is harvested from a mammal with a size and anatomy similar to a human's heart size and anatomy.

4. The heart valve prosthesis of claim 2 wherein the harvested xenograft mitral heart valve has intact chordal extending from the leaflets and a section of papillary muscle attached at the end of the chordae.

5. The heart valve prosthesis of claim 4 wherein the papillary muscle attached to the chordae is reinforced with a reinforcing patch.

6. The heart valve prosthesis of claim 1 further comprising a collar enveloping the end of the annulus of the harvested tissue heart valve.

7. The heart valve prosthesis of claim 6 wherein the collar comprises xenograft pericardial tissue.

8. The heart valve prosthesis of claim 7 wherein the collar is sutured to the inner surface of the annulus and the outer surface of the annulus.

9. The heart valve prosthesis of claim 6 wherein the collar and the sewing rim are formed from an integral section or material.

10. The heart valve prosthesis of claim 1 further comprising a belt around the annulus to provide further support for the annulus.

11. The heart valve prosthesis of claim 10 wherein the belt has a thickness along the annulus surface of at least about 1.2 mm.

12. The heart valve prosthesis of claim 10 wherein the belt comprises a portion of pericardial tissue folded over a ring structure.

13. The heart valve prosthesis of claim 10 wherein the belt comprises rolled up tissue.

14. The heart valve prosthesis of claim 13 further comprising a collar, wherein the collar, sewing rim and belt are formed from a single section of integral material.

15. The heart valve prosthesis of claim 14 wherein the integral material comprises pericardial tissue.

16. The heart valve prosthesis of claim 1 wherein the sewing rim comprises visual markers.

17. The heart valve prosthesis of claim 1 wherein the sewing rim comprises synthetic material.

18. The heart valve prosthesis of claim 1 wherein the annulus comprises pledgeted suture reducing the circumference of the annulus.

19. The heart valve prosthesis of claim 1 wherein the sewing rim projects at least about 2 mm from the surface of the annulus.

20. The heart valve prosthesis of claim 1 wherein the sewing rim extends from about 2.0 mm to about 4 mm from the surface of the annulus.

21. The heart valve prosthesis of claim 1 wherein the sewing rim extends from about 2 mm to about 3.5 mm from the surface of the annulus.

22. The heart valve prosthesis of claim 1 wherein the harvested tissue heart valve comprises unfixed homograft tissues.

23. A method of producing a heart valve prosthesis comprising a harvested tissue heart valve with integral leaflets, the heart valve having an annulus at one end of the valve, the method comprising attaching a sewing rim having an extension of material extending outwardly from the surface of the annulus of the harvested tissue heat valve.

24. The method of claim 23 wherein the sewing rim extends from about 2 mm to about 4 mm from the surface of the annulus.

25. The method of claim 23 wherein the sewing rim is formed from a portion of folded pericardial tissue, the pericardial tissue extending to a collar that envelopes the end of the annulus.

26. The method of claim 25 wherein the pericardial tissue extends to a belt formed by rolling tissue at the end of the pericardial tissue opposite the collar and suturing the rolled tissue to secure the belt.

27. The method of claim 25 wherein the collar is formed by folding pericardial tissue over the end of the annulus and suturing the collar material to the inner surface of the annulus and to the outer surface of the annulus to envelope the end of the annulus.

28. The method of claim 23 wherein the circumference of the sewing rim is selected prior to the attachment of the sewing rim to the harvested heart valve.

* * * * *